United States Patent [19]

Fujimiya et al.

[11] Patent Number: 5,242,567
[45] Date of Patent: Sep. 7, 1993

[54] FLUORESCENT PATTERN READING APPARATUS

[75] Inventors: Hitoshi Fujimiya; Hiromichi Mishima; Toshitaka Ishikawa, all of Yokohama; Kouji Yuda, Tokyo; Hisanori Nasu, Yokohama, all of Japan

[73] Assignee: Hitachi Software Engineering Co., Ltd., Yokohama, Japan

[21] Appl. No.: 704,206

[22] Filed: May 22, 1991

[30] Foreign Application Priority Data

May 22, 1990 [JP] Japan .................................. 2-132048

[51] Int. Cl.$^5$ ..................... G01N 27/26; G01N 27/447
[52] U.S. Cl. ............................ 204/299 R; 204/182.8; 356/344
[58] Field of Search ............ 204/299 R, 182.8, 182.9, 204/182.7; 356/344

[56] References Cited

U.S. PATENT DOCUMENTS

| 4,675,095 | 6/1987 | Kambara et al. | 204/299 R |
| 4,810,348 | 3/1989 | Sarrine et al. | 204/299 R |
| 5,069,769 | 12/1991 | Fujimiya et al. | 204/182.8 |

FOREIGN PATENT DOCUMENTS

| 152786 | 8/1985 | European Pat. Off. |
| 0241904 | 10/1987 | European Pat. Off. |
| 275440 | 7/1988 | European Pat. Off. |
| 284660 | 10/1988 | European Pat. Off. |
| 294996 | 12/1988 | European Pat. Off. |
| 0294996 | 12/1988 | European Pat. Off. |
| 0330120 | 8/1989 | European Pat. Off. |

*Primary Examiner*—John Niebling
*Assistant Examiner*—John S. Starsiak, Jr.
*Attorney, Agent, or Firm*—Fay, Sharpe, Beall, Fagan, Minnich & McKee

[57] ABSTRACT

A fluorescence pattern reading apparatus for reading a fluorescence pattern by exciting a fluorescence substance labeled on a sample developed into an electrophoresis pattern by electrophoresis of the sample has optical scanning mechanisms, a light-receiving unit, a photoelectric converting unit, and amplifiers. The mechanisms are to irradiate the gel in the direction of thickness of the gel by scanning the irradiation light for exciting the fluorescent substance of the fluorescence patter. The light-receiving unit is to receive the fluorescence by separating the fluorescence from the light scattered on the reading surface of the gel due to a spatial position relationship of a light-receiving path in which the light-receiving surface is set to exist in the direction different from the axis of the irradiation light. The photoelectric converting unit is to generate electric signals by converting light signals received by the light-receiving unit. The amplifiers are to generate electric signals of the fluorescence patter in order by amplifying the electric signals from the converting unit by the integral operation in synchronization with the scanning of the irradiation light.

6 Claims, 9 Drawing Sheets

C/D CONTROL SIGNAL

FLUORESCENT PATTERN READING APPARATUS

BACKGROUND OF THE INVENTION

The present invention relates to a fluorescent pattern reading apparatus and, more particularly, to a fluorescent pattern reading apparatus capable of reading a fluorescent pattern by appropriately varying sensitivity to fluorescent patterns of various samples in accordance with characteristics of fluorescence intensity, background light, etc.

Generally, electrophoresis analysis of samples labeled with a radioactive isotope is employed for analysis of the structures of various genes, including DNA sequencing (determination of the sequence of bases of the gene), mass analysis of proteins such as amino acids, and analysis of the structure of a polymer. The electrophoresis analysis involves performing electrophoresis using a gel containing fragments of a sample labeled with a radioactive isotope, transcribing a distribution pattern of fragments developed by the electrophoresis to an X-ray film, and then performing analysis of the distribution pattern.

On the other hand, in recent years, as technology of light sources such as the laser has advanced, there has been developed the electrophoresis analysis of samples labeled with a fluorescent substance, in place of the radioactive isotopes, by using the fluorescence method. The electrophoresis pattern reading apparatus using the fluorescence method presents the advantage that no dangerous and expensive radioactive isotopes are required. In order to allow the electrophoresis pattern reading apparatus using the fluorescence method to achieve a signal-to-noise ratio (a S/N ratio) equal to the electrophoresis analysis using the radioactive isotopes, high technology of an optic system and signal processing technology are required.

Description will be made of a representative example of the electrophoresis pattern reading apparatus by taking a DNA sequencing apparatus as an example. When the DNA sequencing is performed by using the DNA sequencing apparatus, a sample containing a DNA whose structure is to be determined is fragmented by controlling a reaction rate of a chemical reaction specific to the site of each base with a restriction enzyme and labelling the resulting fragments with a fluorescent substance. The fragments are different in length and each of the fragments contains a certain particular base selected from four different bases, i.e. adenine (A), cytosine (C), guanine (G) and thymine (T), at its cut terminal. The fragments of the DNA so fragmented as to contain A, C, G and T are separated in accordance with the lengths of the fragments by electrophoresis, so that the structure of the DNA is determined by performing the electrophoresis to separate the fragments, radiating the separated fragments with laser light, exciting the fluorescent substance labelled on each fragment, measuring the distribution of intensity of the fluorescence emitted from the fluorescence substance, and reading the sequence of the bases.

FIG. 16 is a schematic diagram showing an example of the distribution of the DNA fragments provided by performing the electrophoresis. As the distance of migration by the electrophoresis varies with lengths of the DNA fragments (the difference of their molecular weights), the fragments having the same molecular weights gather together as time elapses, thereby forming an electrophoresis pattern 70 as shown in FIG. 16. The electrophoresis pattern 70 is formed by developing the fragments into each band 66 in accordance with their molecular weights, and the pattern is formed as a whole by developing the sample into each of the bands 66 on lanes 71, 72, 73 and 74 corresponding to each of the four bases. The amount of the sample required by each band is extremely small, as low as 10-16 mol. As difference in molecular weight occurs among the DNA fragments for the bases A, C, G and T by the molecular weight corresponding to one base or more, the distances migrated by the electrophoresis varies with the bands on lanes 71, 72, 73 and 74 for the respective bases. Hence, the bands 66 in the lanes 71, 72, 73 and 74 for the respective bases A, C, G and T are not theoretically disposed transversely in a row with each other. For the DNA sequencing, the sequence of the DNA is analyzed by scanning the order of the bands 66 from the bottom in each of the lanes 71 to 74 for the respective bases A, C, G and T.

As described hereinabove, the analysis by means of the electrophoresis method can be applied to the DNA sequencing apparatus for analyzing the sequence of the bases of a DNA. It can further be noted that the analysis by means of the electrophoresis method can likewise be applied to electrophoresis of other samples. In this case, the sample to be analyzed is subjected to electrophoresis, thereby reading the distribution pattern developed by the electrophoresis. By performing the electrophoresis of the sample to be analyzed, the sample is separated into bands in accordance with its molecular weights or with a charge amount of the sample in a solvent, and the distribution of the resulting bands is read, thereby determining the difference in molecular weight of the samples from the extent to which the bands are distributed. And the molecular weight can be estimated and the presence or absence of a given molecule can be determined by measuring the distance migrated by the electrophoresis of the fragments of the sample and determining the presence or absence of the band in a predetermined position.

In the analysis by electrophoresis, a sample labeled with a fluorescent substance is first poured into a gel serving as a base and the gel is then subjected to electrophoresis. After the completion of the electrophoresis, the gel is provided with a distribution pattern in which the bands are distributed in accordance with the difference in molecular weight among the fragments of the sample, and the distribution of the bands are then measured. The measurement of the distribution of the bands is performed by radiating the electrophorezed gel with a light, such as laser light or lamp light serving as light for exciting a fluorescent substance and measuring the distribution pattern by sensing the fluorescence excited from the gel by a photoelectrically converting element. As the gel, there may be employed, for example, polyacrylamide gel or agarose gel. The sample may be labeled with the fluorescent substance prior to electrophoresis or by drying the gel subsequent to electrophoresis or after the transcription of the sample to a thin film filter from the gel, etc.

As an example of the electrophoresis apparatus of this type using the electrophoresis detecting method, there may be mentioned an electrophoresis apparatus as disclosed in Japanese Patent Laid-open Publication (kokai) No. 62,843/1986 (corresponding to U.S. Pat. No. 4,675,095).

Description will now be made specifically of the electrophoresis apparatus using the fluorescence detecting method.

FIG. 12 is a perspective view showing an outlook of conventional electrophoresis device. As shown in FIG. 12, the conventional electrophoresis device comprises an electrophoresis and instrumentation unit 51 for carrying out electrophoresis and instrumenting the distribution of fluorescence, a data processor unit 52 for processing data instrumented, and a cable 53 connecting them to each other. The electrophoresis and instrumentation unit 51 has a door 51a and the door 51a is opened to pour a gel functioning as a base for electrophoresis of DNA fragments and then a given amount of a sample to be analyzed. Then the door 51a is closed and a switch is turned on to start up electrophoresis. As electrophoresis has been started up, an operational state is displayed and monitored on a display panel 51b of the electrophoresis and instrumentation unit 51. The data instrumented is then transferred to the data processor unit 52 and is subjected to desired data processing in accordance with the preset programs. The data processor unit 52 comprises predominantly a main body of a computer 54 consisting of a microprocessor, memory and so on, a keyboard 55 from which instructions are given by the operator, a display 56 for display of processing results and states, and a printer 57 for recording the processed results.

FIG. 13 is a block diagram showing the construction of the inside of the electrophoresis and instrumentation unit. As shown in FIG. 13, the electrophoresis and instrumentation unit 51 (FIG. 12) comprises an electrophoresis subunit 63 and a signal processor subunit 64. The electrophoresis subunit 63 further comprises an electrophoresis section 5 in which electrophoresis is performed, a first electrode 2a and a second electrode 2b for applying voltage to the electrophoresis section 5, a support plate 3 for supporting the electrophoresis section 5 and the first and second electrode 2a and 2b, a power supply 4 for applying voltage to the electrophoresis section 5, a light source 11 for generating light to excite a fluorescent substance, an optical fiber 12 for leading the light from the light source 11, a condenser 14 of an optic system for condensing and collecting fluorescence 13 generated by the fluorescent substance, an optical filter 15 for selectively passing the light having a particular wavelength therethrough, and an optical sensor 16 for converting the condensed light into electrical signals. The signal processor subunit 64 further comprises an amplifier 17 for amplifying the electrical signals from the optical sensor 16, an analog-digital converting circuit 18 for converting analog signals of the electrical signals into digital data, a signal processing section 19 for implementing pre-processing of the digital data converted, for example, by addition average processing or the like, an interface 20 for implementing the interface processing for feeding the pre-processed data to an external data processor, and a control circuit 10 for performing the entire control of the electrophoresis and the signal processing. The digital signal OUT is generated from the signal processor subunit 64 and then supplied to the data processor unit 52 (FIG. 12), thereby implementing the data processing such as analysis processing and so on.

Description will now be made of the operation of the electrophoresis device which is constructed in the manner as described hereinabove.

Reference is made to FIGS. 12 and 13. After opening the door 51a of the electrophoresis and instrumentation unit 51, a gel is poured into the electrophoresis section 5 disposed within the unit 51 and thereafter a sample of DNA fragments labeled with a fluorescent substance is poured thereinto. A switch of the display panel 51b is turned on to give an instruction for starting electrophoresis, and then voltage is applied from the first and second electrodes 2a and 2b of the power supply 4 to the electrophoresis section 5, thereby starting up electrophoresis. The electrophoresis allows the sample labeled with the fluorescent substance to be migrated in the lanes 71, 72, 73 and 74, thereby gathering the molecules having the same molecular weights together and forming the bands 66, for instance, as shown in FIG. 16. The molecules having smaller molecular weights are allowed to migrate at a rate faster than those having greater molecular weights so that the former are migrated a distance longer than the latter within the same time unit. The bands 66 are detected in a manner as shown in FIG. 14a by leading light from the light source through the optical fiber 12 and irradiating the gel in the transverse direction of the electrophoresis section 5 on its optical path, thereby forcing the labeled fluorescent substance gathered on the bands 66 of the gel to emit fluorescence 13. The fluorescence generated is so very faint because only a very minute amount of the fluorescent substance is present, as small as approximately $10^{-16}$ mole per band although the amount thereof may vary to some extent with the absorptivity of the fluorescent substance, the quantization efficiency, the intensity of the exciting light and so on. When fluorescein isothiocyanate is used as the fluorescent substance, the fluorescein isocyanate has a peak of the exciting wavelength of the exciting light at 490 nm, a peak of fluorescence at 520 nm, a molar absorptivity at $7 \times 10^4$ mol$^{-1}$·cm$^{-1}$, and the quantization efficiency of approximately 0.65.

If the fluorescent substance exists in the amount of $10^{-16}$ mole per band, photons of the fluorescence are produced in the order of $10^{10}$/s when argon ion laser is employed as the exciting light at the output of 1 mW at 480 nm although the light quantity of the fluorescence varies with the thickness of the gel and so on. Further, it is to be noted that the fluorescence spreads in all peripheral directions so that it is difficult to receive the light directly by a general CCD solid state image pick-up element camera or the like.

Referring to the front view as shown in FIG. 14a and to the longitudinally sectional view as shown in FIG. 14b, the electrophoresis section 5 comprises a gel 5a consisting of polyacrylic amide or the like and gel supporting members 5b and 5c made of glass for supporting and interposing the gel 5a from both sides. For example, a sample of DNA fragments is poured into the gel 5a of the electrophoresis section 5 from its upper portion and electrophoresis is carried out by applying voltage to the first electrode 2a and the second electrode 2b (FIG. 12). Light radiated from the light source, for example, laser light, passes through the light path 61 in the gel 5a from the optical fiber 12 and is irradiated to the fluorescent substance on the light path 61. This allows the fluorescent substance present on the light path 61 to be excited to emit fluorescence 13. The fluorescence 13 emitted is led to a substage condenser or light collector 14 of optics consisting of a combination of lenses and then selected by the optical filter 15 after being condensed, thereby converting it into electrical signals by means of the one-dimensionally optical sensor 16. In order to efficiently convert the faint light into electric signals, the image is converted into the electric signals by the optical sensor 16, such as the one-dimensionally optical sensor of the CCD, by optically amplifying the image to $10^4$ to $10^5$ times by an image intensifier or the like. The electrical signals obtained by the optical sensor 16 are amplified to a desired level by the amplifier 17 and subjected to analog-digital conversion by the analog-digital circuit 18 followed by supply to the signal processing section 19. The signal processing section 19 processes the signals by means of addition-average processing or the like in order to improve a signal-to-noise ratio (a S/N ratio). The data of the digital signals which has been subjected to signal processing is fed to the data processor subunit 52 through the interface 20.

FIGS. 15a and 15b are views describing an embodiment of signals indicative of a fluorescence intensity pattern of the DNA fragments to be transferred from the electrophoresis and instrumentation subunit 51. For instance, as shown in FIG. 15a, as the laser light is irradiated upon the electrophoresis section 5 in which the electrophoresis is performed, the fluorescent substance of the gel present on the light path 61 is excited to emit fluorescence 13. This fluorescence 13 is detected in predetermined detection positions in each lane in the direction of electrophoresis in the course of a lapse of time. This allows the fluorescence 13 to be detected when the bands 66 in each lane pass through the positions on the light path 61, thereby detecting a pattern signal of fluorescence intensity in each lane, as shown in FIG. 15b. Therefore, the pattern signal of the magnitude of fluorescence intensity as shown in FIG. 15b is represented as a pattern signal of fluorescence intensities of the bands 66 in the electrophoresis direction 62.

The data processor unit 52 performs data processing for comparing molecular weights and determining the sequence of DNA from data of the pattern of fluorescence intensity. The sequence of the bases or the like determined by data processing is symbolized and then generated, thereby being displayed on a display screen 56 or printed by a printer 57. The data of the result obtained by data processing may be recorded in magnetic recording media as needed.

It is to be noted herein that, as described hereinabove, the electrophoresis pattern reading apparatus using the fluorescence detecting method is so constructed that the light is irradiated upon the electrophoresis section in the transverse direction from the light source, thereby providing the exciting light. The incidence of the light from the side has the advantage that the sensitivity with which the gel receives the fluorescence through the glass of the gel supporting plate becomes high because the gel is irradiated with the light directly from the light source so that the glass of the gel supporting plate is not exposed to the exciting light from the light source so that the light does not scatter from the exciting light.

However, when for example agarose gel is employed as the gel for the electrophoresis section, a degree of scattering the exciting light in the gel occurs so that it is difficult to keep the size and the strength of the spot light of the light beam of the exciting light uniform over the entire length of the light path 61. In other words, the light intensity is high on the side of the light path 61 which the exciting light strikes while the intensity of the light becomes lower as the light proceeds within the gel. Further, if bubbles were to form at the end portions of the electrophoresis section which are not involved with electrophoresis when the gel is poured prior to the electrophoresis, it is difficult to let the exciting light strike the gel or a large degree of scattering may happen when the bubbles exist on the light path 61 for the exciting light. Furthermore, when the light is irradiated in the transverse direction, all the fluorescent substance-labeled bands located on the light path are caused to emit fluorescence simultaneously. Accordingly, in this case, there must be employed, as an optical sensor for receiving and converging the very faint fluorescence, a combination of an image intensifier and a CCD camera or an expensive one-dimensional optical sensor (a line sensor) of high sensitivity such as a CCD camera so modified as to equivalently increase its sensitivity by cooling the CCD solid state image pick-up element in order to reduce dark current.

It is also to be noted that such an electrophoresis pattern reading apparatus suffers from the disadvantages that it is of a type capable of reading the electrophoresis pattern during the electrophoresis so that it is not suitable for reading fluorescence patterns other than those for determining the base sequence of DNA.

SUMMARY OF THE INVENTION

The present invention has the object to provide a fluorescence pattern reading apparatus capable of reading various samples labeled with a fluorescent substance and transcribed to various gel materials or a thin layer.

In order to achieve the aforesaid object, the present invention consists of a fluorescence pattern reading apparatus for reading a fluorescence pattern emitting fluorescence by subjecting a sample to electrophoresis, developing the sample into an electrophoresis pattern, labeling the sample with a fluorescent substance and emitting the fluorescence by exciting the fluorescent substance, comprising optical scanning means for irradiating the fluorescence pattern with an irradiation light for exciting the fluorescent substance of the fluorescence pattern in a direction of thickness of a gel; light receiving means for receiving the fluorescence of the fluorescence pattern by separating the fluorescence from light scattered from a reading surface by means of a spatial relationship of a light-receiving path so set as to allow its light-receiving surface to exist in a direction different from a light axis of the irradiation light; photoelectrical converting means for outputting electric signals by photoelectrically converting optical signals received by a light-receiving unit; and an amplifier for outputting electric signals of the fluorescence pattern in order by amplifying the electric signals from the photoelectric converting means by performing an integral operation in synchronization with scanning with the irradiation light.

The amplifier comprises an operational amplifier, a condenser and a switch for controlling the integral operation wherein the electric signals from the photoelectric converting unit are subjected to integral amplification by a portion corresponding to a reading pixel in order by controlling the integral operation of an integral circuit in synchronization with the scanning with the irradiation light by the optical scanning means, thereby outputting the electric signals for the fluorescence pattern.

As described hereinabove, the fluorescence pattern reading apparatus is provided with the optical scanning mechanism, the light receiving unit for receiving the fluorescence of the fluorescence pattern, the photoelectric converting unit, and the amplifier. The light-receiving unit is so arranged as to receive the fluorescence of the fluorescence pattern by separating it from the light scattered on the reading surface of the gel due to a spatial relationship of the light-receiving path so set as to allow the light-receiving surface to exist in the direction different from the light axis of the irradiation light, and the photoelectric converting means converts the optical signals received by the light-receiving unit photoelectrically into electric signals. The amplifier has an integral circuit and amplifies the electric signals from the photoelectric converting unit in order by performing integral operation in synchronization with the scanning of the irradiation light, thereby generating the electric signals of the fluorescence pattern.

The integral circuit in the amplifier has the operational amplifier, the condenser and the switch for controlling the integral operation arranged so as to perform integral operations for faint signals with high accuracy. The control of the integral operation of the integral circuit is performed in synchronization with the scanning of the irradiation light by the optical scanning mechanism, and the electric signals from the photoelectric converting unit are subjected to integral amplification by a portion corresponding to the reading pixel, thereby generating the electric signals of the fluorescence pattern.

The optical scanning mechanism performs flying spot scanning of the fluorescence pattern by scanning the light in the reading direction from the front side of the reading surface. The amplifier with the integral circuit performs the integral amplification of light signals of faint fluorescence in response to the output of the sensor from the light-receiving unit in synchronization with the operation of the driving circuit for controlling the scanning angle of a scanning mirror. The integral amplification controls the integral circuit and performs amplification to accumulate the charges in the condenser for a predetermined period of time, thereby improving the signal-to-noise ratio. This system can thus read the fluorescence pattern of the sample labeled with the fluorescence by the flying spot scanning. This system can further read minute regions in order even for a gel from which the light scatters to a large extent, such as agarose gel, or a sample transcribed to the thin layer filter, so that the reading can be performed with a high signal-to-noise ratio.

When the fluorescence pattern of a sample transcribed to the thin layer filter is read, the level of the light scattered from the thin layer filter is high, so that the reading can be performed with the background light containing the scattering light reduced by immersing the thin layer filter and then interposing its both sides between the gel supporting plates.

The exciting light for reading the fluorescence pattern is irradiated in the direction of thickness of the gel so that the area to be irradiated with the light is not caused to be spread due to the light scattered from the gel. Further, the gel can be read after drying or, when the sample is read after transcription to the thin layer filter, the reading can be performed in the same manner as for the gel alone while suppressing the adverse influence of the background light from the thin layer filter, so that the fluorescence pattern can be read with a high signal-to-noise ratio.

Furthermore, this system according to the present invention can read the fluorescence pattern in accordance with the size of the sample by synchronizing the scanning operation with the sampling operation of the integral circuit of the amplifier following from light-receiving unit. Hence, this system can save the reading time. By controlling the time interval of the sampling operation, the time for the integral operation and so on, a ratio of the fluorescence from the labeled sample to the background light can be made high, thereby reading the fluorescence pattern of the sample with ease and high sensitivity.

DESCRIPTION OF THE PREFERRED EMBODIMENTS

Figure 1:
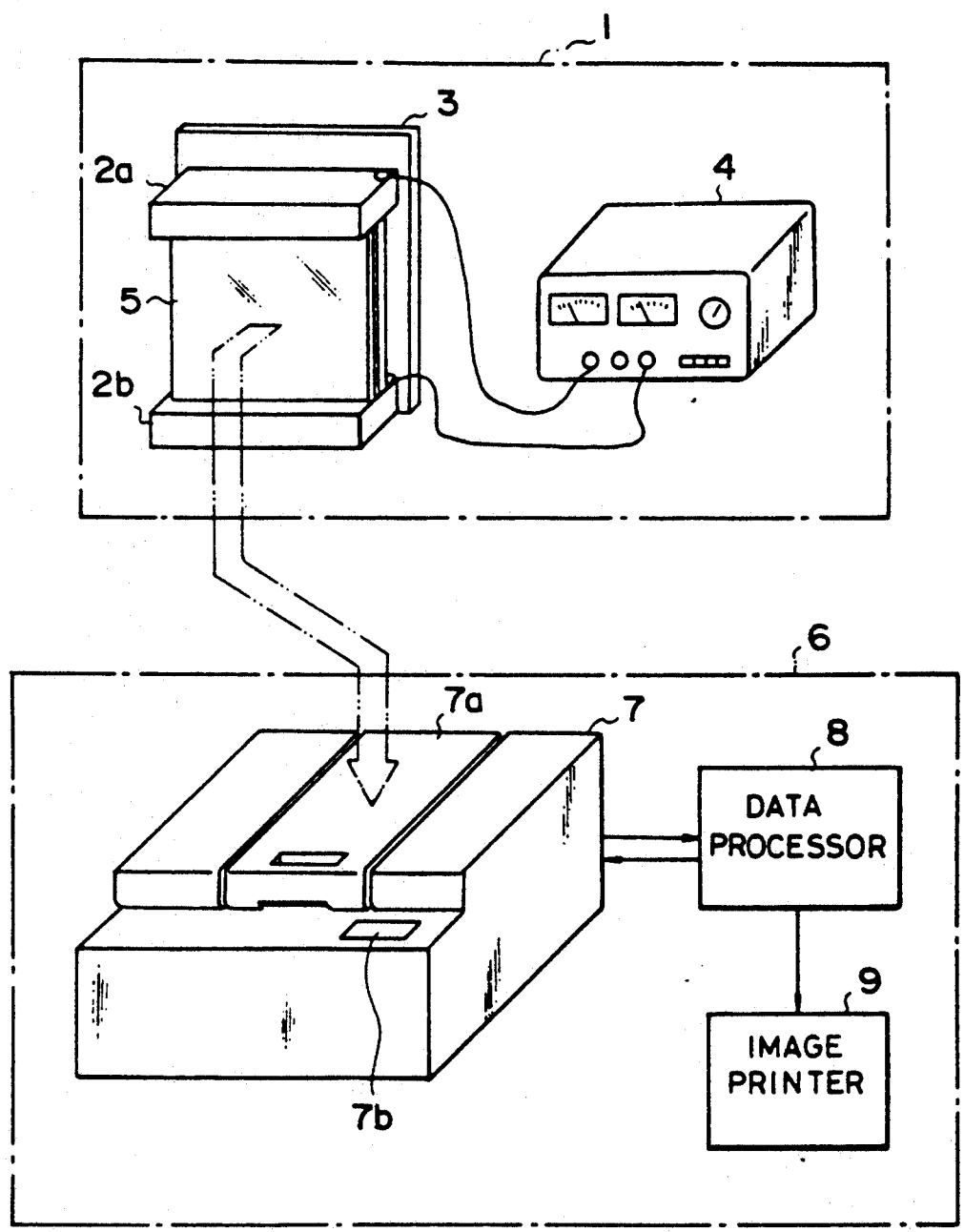
FIG. 1 is a diagrammatic representation of an overall construction of the electrophoresis pattern reading apparatus of the fluorescent type according to an embodiment of the present invention.
Figure 14A:
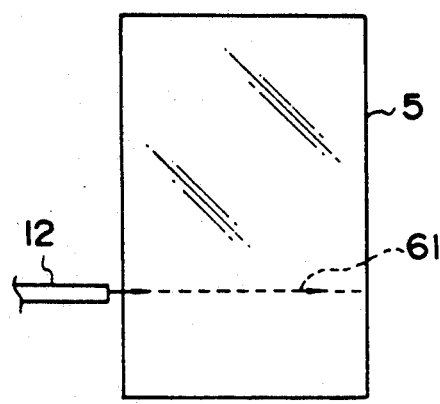
FIGS. 14a and 14b are front and longitudinally sectional views showing the electrophoresis section for describing the principle of the operation for detecting the electrophoresis pattern by the fluorescence method.
Figure 14B:
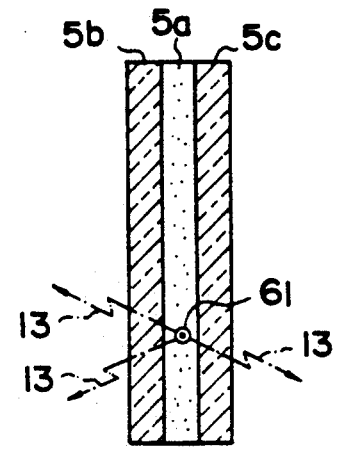
Figure 15A:
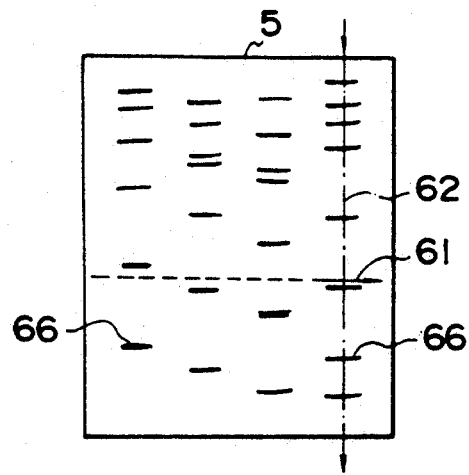
FIGS. 15a and 15b are schematic diagrams showing signals of a pattern of the intensity of fluorescence of DNA fragments to be sent from the electrophoresis and instrumentation units.
Figure 15B:
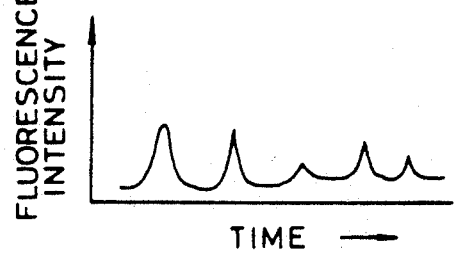
Figure 16:
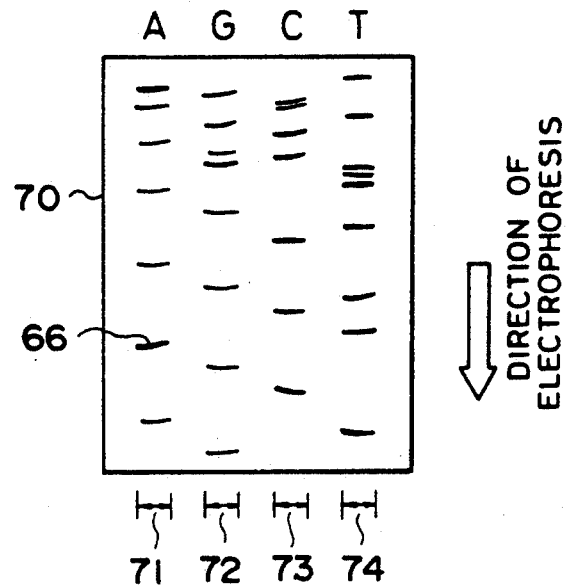
FIG. 16 is a view showing an example of the distribution of the DNA fragments developed by electrophoresis.

FIG. 1 diagrammatically represents the overall construction of the electrophoresis pattern reading system of fluorescent type according to an example of the present invention. As shown in FIG. 1, the electrophoresis pattern reading system of fluorescent type is overall constructed such that an electrophoresis unit 1 is disposed separately from a reading unit 6. The electrophoresis unit 1 comprises a migration subunit 5 composed of a gel functioning as a base for electrophoresis and a gel-supporting body for supporting the gel, a first electrode 2a and a second electrode 2b for applying electrophoresis voltage to the mounted migration subunit 5 (hereinafter referred to as a migration section), a supporting plate 3 for supporting the first electrode 2a and the second electrode 2b as well as the migration section 5, and a power supply 4 for supplying the electrophoresis voltage. The migration section 5 comprises the gel such as polyacrylamide or the like on which a sample for electrophoresis is developed and the gel-supporting body, such as a pair of glass plates disposed so as to interpose the gel from both sides, as described hereinabove (and as shown in FIGS. 14a and 14b). In the electrophoresis unit 1, the migration section 5 is mounted and a sample of fragments subject to electrophoresis is supplied from an upper portion of the gel in the migration section 5. Thereafter, the migration voltage is applied to the first electrode 2b and the second electrode 2b from the power supply 4, thereby starting up electrophoresis. After electrophoresis, the migration section 5 is removed from the electrophoresis unit 1 and then mounted to the reading unit 6.

The reading unit 6 is to perform data processing by mounting the migration section 5 after electrophoresis as it is (or with the gel removed from the migration section 5). As shown in FIG. 1, the reading unit 6 is composed of an instrumentation subunit 7 as a major component, with a data processor unit 8 and an image printer 9 added thereto. The data processor unit 8, the image printer 9 and so on are arranged so as to generate the electrophoresis pattern data read by the instrumentation subunit 7 after data processing, image processing and judgment processing. To the instrumentation subunit 7 is mounted the migration unit 5 (the migration unit composed of the gel and the gel-supporting body) after electrophoresis has been performed in the electrophoresis unit 1, and a reading base is disposed immediately underneath a lid 7a at an upper portion of the instrumentation subunit. The migration section 5 is mounted to the reading base of the instrumentation subunit 7 by opening the lid 7a. After the migration section 5 has been mounted, the lid 7a is closed and a switch on an operational display panel 7b for starting up the reading operation is then pressed, whereby the instrumentation subunit 7 starts up the reading of the electrophoresis pattern of the gel of the migration section 5. As the reading of the electrophoresis pattern starts up, the gel of the migration section 5 mounted is irradiated with exciting light from a light source in the instrumentation subunit 7, to excite the fluorescent substance and the distribution of the fluorescent substance is computed by receiving the fluorescence. The data processor unit 8 is to process data on the basis of the read data that has been computed by the instrumentation subunit 7 and to control the instrumentation subunit 7. The data processed is visualized by the image printer 9 or the like.

Figure 2:
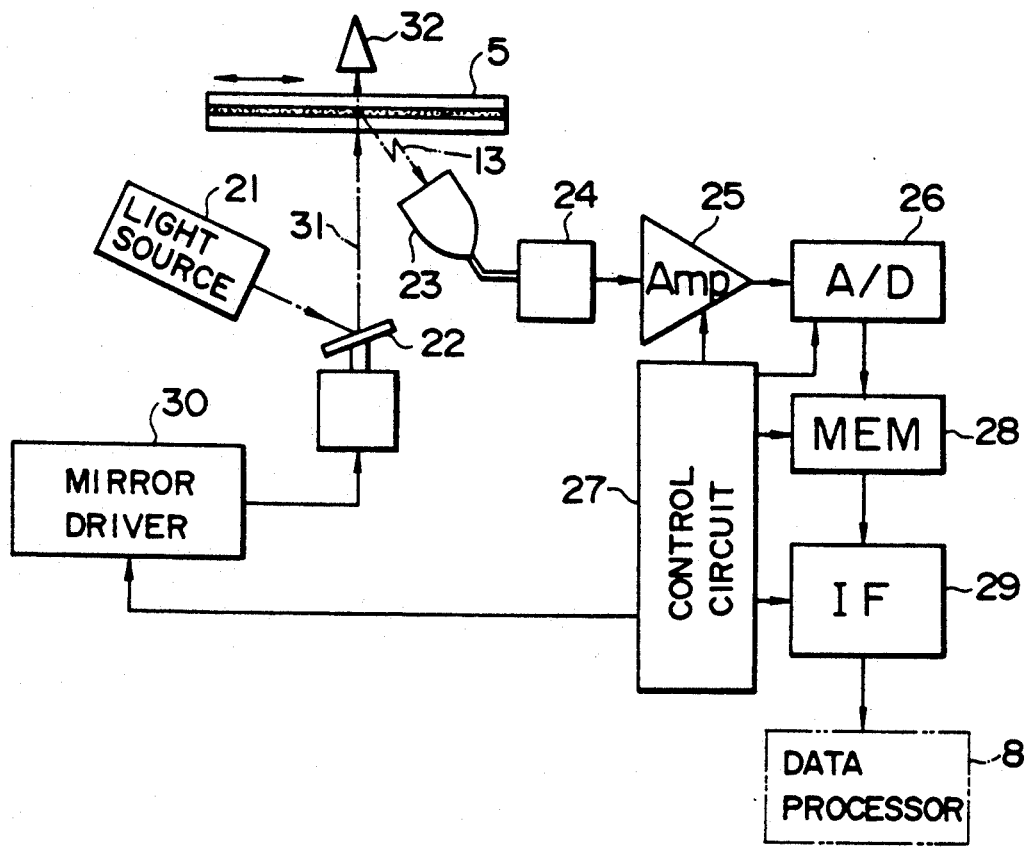
FIG. 2 is a block diagram showing the construction of an essential portion of an instrumentation unit.
Figure 3:
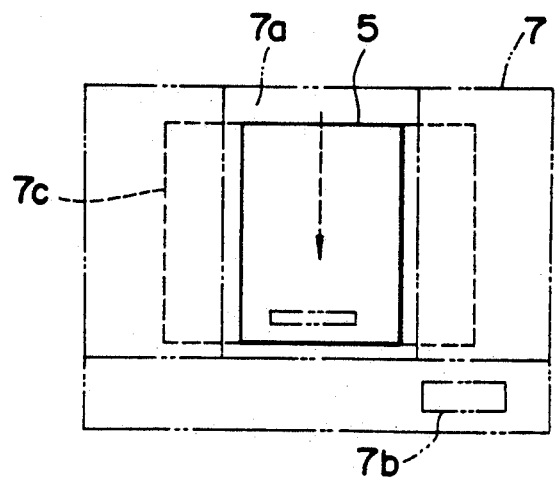
FIG. 3 is a view showing the position in which the migration unit to be mounted to the instrumentation unit is mounted.

FIG. 2 is a block diagram showing the construction of the essential portion of the instrumentation subunit, and FIG. 3 is a view showing the position in which the migration section is mounted to the instrumentation subunit. Description will be made with reference to FIGS. 2 and 3.

In performing electrophoresis analysis of a sample by using the electrophoresis pattern reading system, the sample labeled with the fluorescent pigment is first subjected to electrophoresis using electrophoresis unit 1. After electrophoresis for a given period, the migration section 5 is removed from the electrophoresis unit 1. Thereafter, the gel of the migration section 5 is placed on an upper portion of the reading base 7c in the instrumentation subunit 7 after opening the lid 7a of the reading unit 6 at the upper portion of the instrumentation subunit 7. The migration section 5 is either mounted wholesale, or with the glass supporting plates removed, as shown in FIG. 3. Then the lid 7a is closed. This concludes the setting to the instrumentation subunit 7. At this time, if the gel is not yet labeled with the fluorescent pigment, the processing for labeling the sample with the pigment is executed. Further, the processing of drying the gel is also executed.

The operation of giving an instruction of the start-up of reading the electrophoresis pattern will now be performed. The operation of starting the reading is executed by giving a start-up instruction by means of pressing the switch of the operation display panel 7b for starting the reading or from the data processor unit 8. In starting the operation of reading by the data processor unit 8, the state in which the migration unit is mounted to the instrumentation subunit 7 is fed to the data processor unit 8 through a control signal line, and the operation of the instrumentation subunit 7 is controlled by the data processor unit 8 in accordance with the state. In this case, the operation of starting up the reading is automatically executed, thereby reducing the burden of operating the switch on the side of the operator.

The distribution data of the fluorescent pigment read is transferred to the data processor unit 8. The data processor unit 8 executed desired processing such as detecting peaks of fluorescence intensity, determining the migration distance, etc., in accordance with preset programs. The result data obtained by data processing are printed out, as needed, by the image printer 9 as an image of the fluorescence intensity with light and shade or as an image in which the fluorescence intensity is grouped by contour lines or by colors or the strength of color. The image is similar to a radioactive X-ray film image which has conventionally been used. The result data which has been data-processed is stored, as needed, as digital data by a magnetic or optical recorder.

FIG. 2 is a block diagram showing the configuration of the instrumentation unit. Laser beam 31 emitted from the light source 21 is scanned by a vibrating mirror 22 drivable by a mirror driver 30 in the direction vertical to the drawing and added to the gel of the electrophoresis unit 5 to be the object for reading. The spot light of the laser beam 31 scanned by the vibrating mirror 22 irradiates the gel of the electrophoresis unit 5 in the direction of thickness while moving along the gel. The fluorescence 13 is emitted from the gel of the electrophoresis unit 5 irradiated with the spot light of the laser beam 31 and the fluorescence 13 is collected by a light collector 23. The light collector 23 collects the fluorescence 13 so that the light axis of a path receiving the fluorescence 13 is different from the light axis of the spot light irradiated on the electrophoresis unit 5, and so that a spatial position relationship of the optical path for receiving the light is composed by the optic lens system, thereby enhancing the sensitivity to detection of light scattered from the face of the electrophoresis unit 5 upon which the light is irradiated. The light collected by the light collector 23 is converted into electric signals by the photoelectric converting unit 24 and amplified by an amplifier 25. On the side opposite to the face of the electrophoresis unit 5 upon which the laser beam 31 is irradiated is mounted a light trap 32 in order to cause the laser beam 31 transmitted through the gel to exert no adverse influence as stray light.

The fluorescence 13 to be detected is received by the light collector 23 by enhancing the light-receiving sensitivity, and the fluorescence 13 received is then converted into electric signals by the photoelectric converting unit 24 followed by input of the electric signals into the amplifier 25. The electric signals amplified by the amplifier 25 are then inputted into an analog-digital converting circuit 26 and converted into digital data. The signals converted into the digital data are stored by a memory 28 and the digital data stored by the memory 28 are then transmitted to a data processor 8 through an interface 29. Overall control of the signal processing is performed by a control circuit 27.

Detailed description will be made of each of the configurations of the instrumentation unit (FIG. 2) of the electrophoresis pattern reading apparatus having the configuration as described hereinabove.

Figure 4:
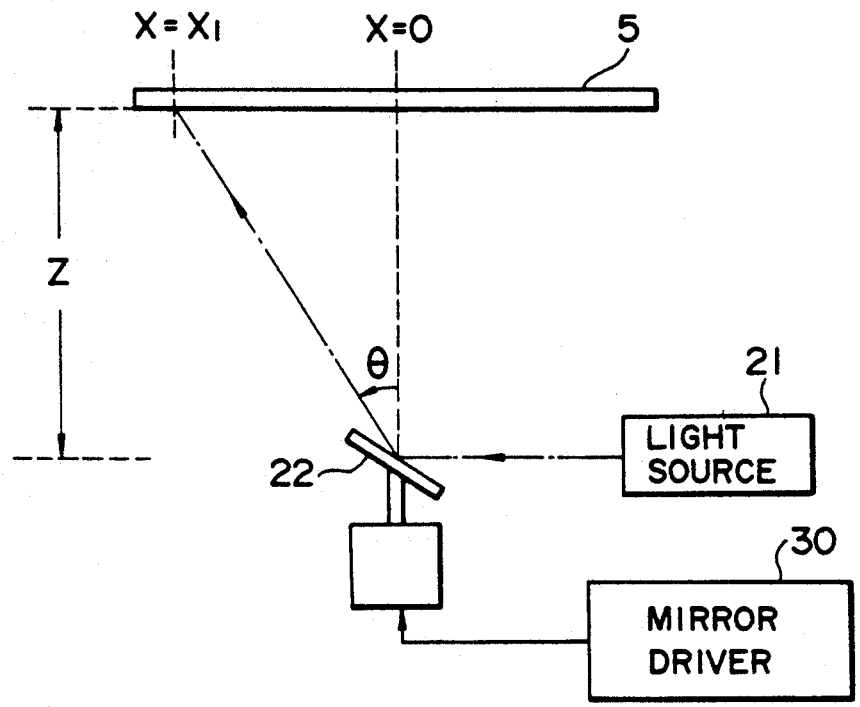
FIG. 4 is a view showing the optical scanning mechanism for scanning the gel surface with laser beam by means of the vibrating mirror.

FIG. 4 is a schematic diagram showing an optical scanning mechanism for scanning the gel surface with a laser beam by using the vibrating mirror.

Figure 5:
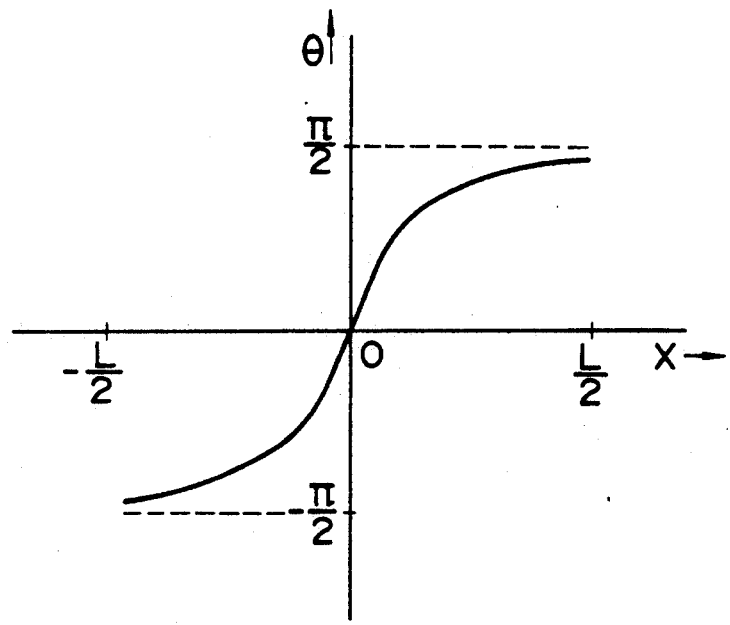
FIG. 5 is a view showing the relationship between the angle of rotation of the vibrating mirror and the travelling distance of the spot light of the laser beam.

The light source 21, the vibrating mirror 22 and the electrophoresis unit 5 are disposed in the positions as illustrated in FIG. 4, so that the velocity at which the spot light moves becomes faster at both end portions of the electrophoresis unit 5 than in the vicinity of the central portion (X=0) thereof when the vibrating mirror 22 is so driven by the mirror driver 30 as to vibrate at equal angular velocities. Hence, the difference in sensitivity to the fluorescence to be detected from the sample occurs between the central portion and both end portions thereof. Therefore, in accordance with the present invention, the velocity at which the vibrating mirror 22 is driven is corrected so as to make constant the velocity of the travelling spot light of the laser beam on the gel of the electrophoresis unit 5. In other words, the relationship of the position X of the spot light with the angle $\theta$ of the mirror is as shown in FIG. 5, and the distance Z between the center of rotation of the vibrating mirror and the central portion of the electrophoresis unit 5 is related to X and $\theta$ by the following formula:

$$\theta = \tan^{-1} X/Z$$

where

Z is the distance from the center of rotation of the vibrating mirror 22; and

X is the distance in the planar direction extending from the point of intersection of a line drawn perpendicular to the gel surface of the electrophoresis unit 5 from the center of rotation of the vibrating mirror 22.

The method for the correction of the rotating angle and the travelling distance in the optical scanning mechanism of this kind may be carried out by using an f$\theta$ lens. However, the f$\theta$ lens is so expensive and a device for mounting the f$\theta$ lens is so heavy that the angle for rotating the vibrating mirror and the travelling distance of the optical scanning mechanism are corrected by providing the mirror driver 30 with a control circuit so arranged as to make control over the angular velocity for rotating the vibrating mirror 22 variable, thereby correcting the velocity at which the rotation of the vibrating mirror 22 is driven.

Figure 6:
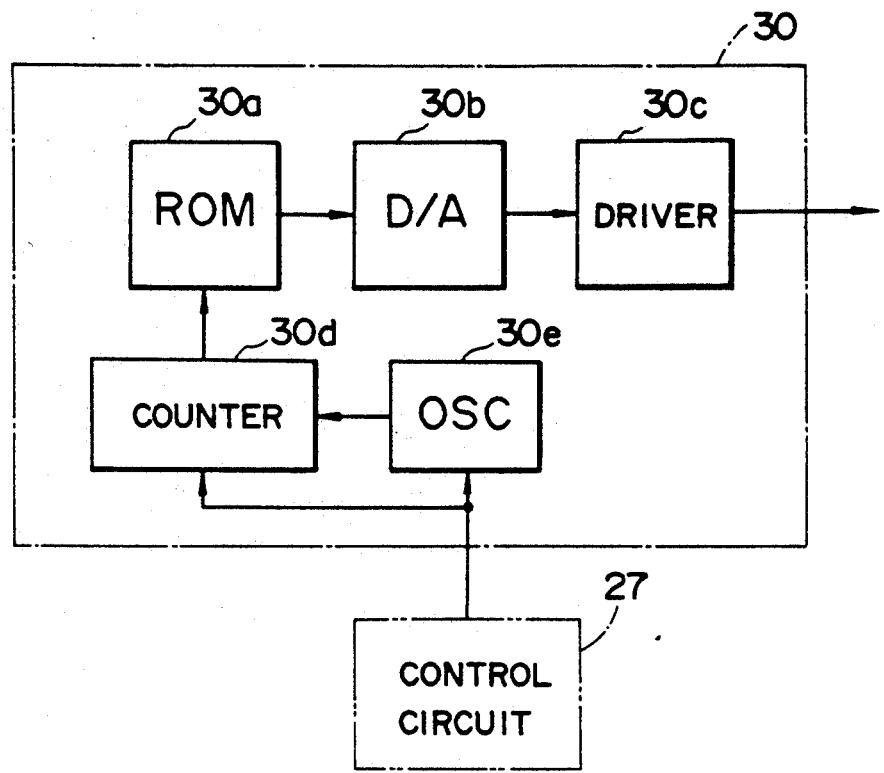
FIG. 6 is a block diagram showing the configuration of the essential portion of the control circuit of the mirror driver for controlling the rotation of the vibrating mirror.

FIG. 6 is a block diagram showing the configuration of the essential portion of the control circuit of the mirror driver for performing the control of the driving of the rotation of the vibrating mirror. As an actuator for the vibrating mirror is employed a straight motor, and the angle of rotation of the vibrating mirror is controlled by applying voltage in proportion to the angle of rotation. In order to allow the spot light of the laser beam to travel at a constant velocity on the surface of the gel, the distance X of the surface irradiated is so controlled as to be in proportion to the time t. The relationship of the angle $\theta$ at which the vibrating mirror rotates with the distance X in which the spot light travels is as shown in FIG. 5. Therefore, signals are generated which have a voltage wave form as corresponding to the graph of FIG. 5 in which the axis of ordinate is represented by time while the axis of abscissa is represented by voltage, and the signals are employed as control signals for driving the vibrating mirror. The control signals are generated by the control circuit for the mirror driver 30 and fed to the actuator of the vibrating mirror 22, thereby performing the control of driving the vibrating mirror 22.

As shown in FIG. 6, the mirror driver 30 comprises a read-only memory 30a for storing a functional wave form, a digital-analog converting circuit 30b for converting the read functional data into voltage signals, a driver 30c for amplifying the voltage signals and generating the amplified voltage signals as control signals for driving the vibrating mirror, a counter 30d for providing the memory with reading addresses in time series, and an oscillating circuit 30e for providing the counter with clock signals.

The oscillating circuit 30e starts operating by an instruction from the control circuit 27 of the instrumentation unit, and the clock signals are inputted into the counter 30d from the oscillating circuit 30e. The counter 30d counts the clock signals as well as generates the reading addresses in time series to be supplied to the read-only memory 30a. As the reading addresses generated by the counter 30d are supplied to the read-only memory 30a in time series, the functional data stored in advance is read in order from the read-only memory 30a. The functional data (FIG. 5) on the angle of rotation of the vibrating mirror is written in advance in the read-only memory 30a and the functional data is read in time series. In this example, the number of bits of the functional data is 12 bits and the functional data to be read are converted by the digital-analog converting circuit 30b into voltage signals as analog signals for controlling the angle of rotation of the vibrating mirror. The voltage signals are supplied by the driver 30c to the vibrating mirror 22 as control signals for driving the vibrating mirror 22 by removing noise in the step form by filtering and amplifying the voltage. This arrangement can vibrate the vibrating mirror at a desired angle of rotation so as to make the velocity of scanning by the spot light of the laser beam on the electrophoresis unit constant.

The scanning velocity is divided into equal parts so as to be variable at 0.5 Hz, 1 Hz, 2 Hz, 5 Hz, 10 Hz, 20 Hz, 50 Hz, 100 Hz and 200 Hz. This is because the reading is performed efficiently by varying the reading velocity in accordance with the difference in amount of the fluorescent substance labeled on the sample to be electrophoresed and with efficiency in quantization. The instruction on the scanning velocity in this case can be given by an operation display panel 7b or the data processor 8, and it is transmitted from the control circuit 27 to the mirror driver 30, thereby controlling the counter 30d and the oscillating circuit 30e and driving the vibrating mirror 22 at a desired scanning velocity.

By controlling the driving of the vibrating mirror 22 in the manner as described hereinabove, the laser beam from the light source is scanned and irradiates the electrophoresis unit 5 as a spot light travelling at a constant velocity. The irradiation of the laser beam excites the fluorescent substance labeled on the gel of the electrophoresis 5 at the portions which have been irradiated with the laser beam, thereby emitting the fluorescence 13 (FIG. 2).

Figure 7:
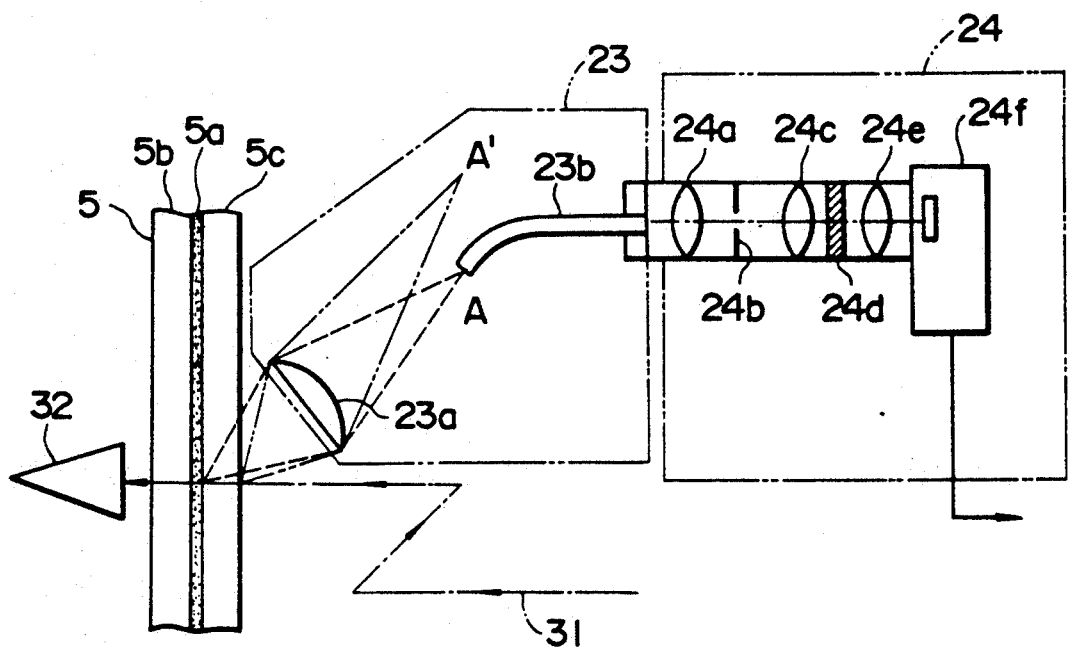
FIG. 7 is a view showing the detailed configuration of the optical system of the light collecting unit and the photoelectric converting unit.

FIG. 7 is a schematic diagram showing the configuration of the essential portions of the light collector for receiving the fluorescence emitted from the gel and the photoelectric converting unit.

As described hereinabove, the gel 5a of the electrophoresis unit is interposed between and supported by gel supporting members 5b and 5c made of glass. As the gel supporting members 5b and 5c referred to herein for the electrophoresis unit 5 in this embodiment, there may be employed boron silicate glass that is relatively non-fluorescent. In addition, quartz glass and other various optic glass may be employed for the gel supporting members 5b and 5c.

Once the electrophoresis unit 5 is irradiated with and scanned by the laser beam 31, the laser beam 31 is transmitted through the gel supporting members 5b and 5c in the direction of thickness, thereby reaching the gel 5a. The laser beam 31 is then transmitted and proceeds through the gel 5a in the direction of thickness. The thickness of each of the gel supporting members 5b and 5c is as thin as approximately 5 mm while the thickness of the gel 5a is set to be as thin as approximately 0.35 mm. The intensity of the laser beam 31 irradiated in the direction of thickness of the gel supporting members 5b and 5c and reaching the gel 5a is nearly equal in every position of the electrophoresis unit 5. The spread of the laser beam 31 and a decrease in the intensity thereof to be caused by scattering at the plane of incidence of the gel 5a and the gel supporting members 5b and 5c can be reduced to a great extent because the laser beam 31 enters in the direction of thickness thereof. It is to be noted herein that the laser beam 31 after transmission through the gel is so arranged as to enter the light trap 32 and to be damped therein so as to cause no adverse influence as stray light.

The fluorescence 13 emitted from the inside of the gel 5a by scanning the gel with the exciting light is collected by the light collector 23 together with the light scattered by irradiation with the exciting light. The scattered light emitted in the gel supporting members 5b and 5c is optogeometrically separated due to a spatial position relationship of the light-receiving path, and only the fluorescence from the gel is transmitted to the photoelectric converting unit 24. In the photoelectric converting unit 24, any other scattered light and the fluorescence emitted within the gel are separated by using an optic filter, and faint fluorescence is converted into electric signals by a photomultiplier. The details of the configuration of the optic system in the light collector 23 and the photoelectric converting unit 24 is as shown in FIG. 7.

Referring to FIG. 7, the fluorescence 13 emitted from the electrophoresis unit 5 and the light scattered from the exciting light emitted from the gel supporting members 5b and 5c reach a cylindrical lens 23a and form an image on the side opposite to the cylindrical lens 23a, as shown in FIG. 7. In the drawing, the point A is a focus for the fluorescence 13 from the gel 5a and the scattered light from the exciting light emitted from the gel 5a. On the other hand, the scattered light from the exciting light emitted from the surfaces of the gel supporting members 5b and 5c forms its image, for example, at a focus A'. It is to be noted herein that the fluorescence can be separated from the scattered light from the gel supporting members photogeometrically due to the spatial position relationship of the light-receiving path by disposing an optical fiber array 23b in the position coinciding with the point A so as to receive the fluorescence from the gel 5a. In the process for irradiating the gel with a laser beam in the direction of thickness of the gel, a very small amount of the scattered light emits on the boundary surface between the gel and the gel supporting members because the refractive index of the gel is approximately 1.4 to 1.5 and comparably close to that of the gel supporting members and the boundary surface between the gel and the gel supporting members is very tight. Hence, the light received at the point A is composed of a great amount of the fluorescence 13 only from the gel 5a and a very small amount of the scattered light of the exciting light emitted from the surface of the gel 5a.

The scattered light emits in substantially the same amount from the gel surface as when the gel 5a is exposed directly to irradiation, whether either or both of the gel supporting members 5b or 5c are removed. In this case, however, a glass plate of a reading base of the instrumentation unit 7 on which the gel is placed can achieve effects similar to the glass of the gel supporting members by its thickness, so that the fluorescence can be detected from the gel surface with certainty. In particular, at this time, when removal of the gel supporting members 5b and 5c is not required because of processing for coloring the gel 5a with a pigment, etc., it is preferred to read the gel 5a with the gel supporting members 5b and 5c attached thereto because the signal-to-noise ratio can be improved.

The fluorescence collected by the optical fiber array 23b is led through the optical fiber and inputted into the photoelectric converting unit 24. Only the parallel light components of the fluorescence inputted into the photoelectrically converting unit 24 are extracted by using a first lens 24a, a diaphragm 24b and a second lens 24c and are allowed to enter an optical filter 24d which removes the components of the scattered light. The fluorescence is then collected by a third lens 24e, led to a photomultiplier 24f which in turn converts the detected fluorescence into electric signals. In the photoelectric converting unit 24, the parallel light components alone pass by the second lens 24c and are allowed to enter through the optical filter 24d in order to improve the efficiency of wavelength separation for the optical filter 24d. And the scattered light of the exciting light occurring in the inside of the gel is separated by the optical filter 24d to thereby improve the signal-to-noise ratio, followed by collecting the light by the third lens 24e and leading to the photomultiplier 24f.

The fluorescence led to the photomultiplier 24f after it has been received and collected, and after the scattered light has been removed by the optical filter, is then converted into electric signals by the photomultiplier 24f and the resulting electric signals are inputted into the amplifier 25. The amplifier 25 amplifies the faint signals to a sufficient extent in amplifying stages containing an integral circuit.

Figure 8:
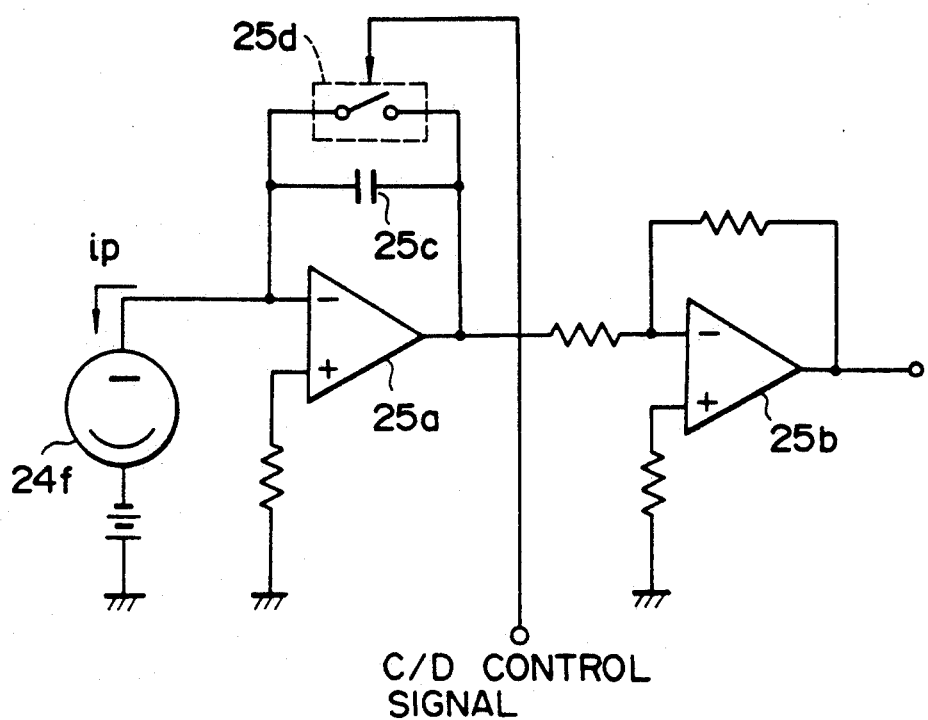
FIG. 8 is a circuit diagram showing the circuit configuration of the amplifier containing the integral circuit.

FIG. 8 is a circuit diagram showing the configuration of the amplifier containing the integral circuit. As shown in FIG. 8, the amplifier 25 has the integral circuit composed of an operational amplifier in its front stage and an output amplifying circuit composed of an operational amplifier in its next stage. The electric signals from the photomultiplier 24$f$ are inputted into the operational amplifier 25$a$ which constitutes the integral circuit together with a condenser 25$c$ and a switch 25$d$ for controlling the integral operation. The output of the integral circuit is inputted into the operational amplifier 25$b$, thereby amplifying the output with a gain to be determined by an outside resistance and thereafter transmitting to an analog-digital converting circuit which follows.

Figure 9:
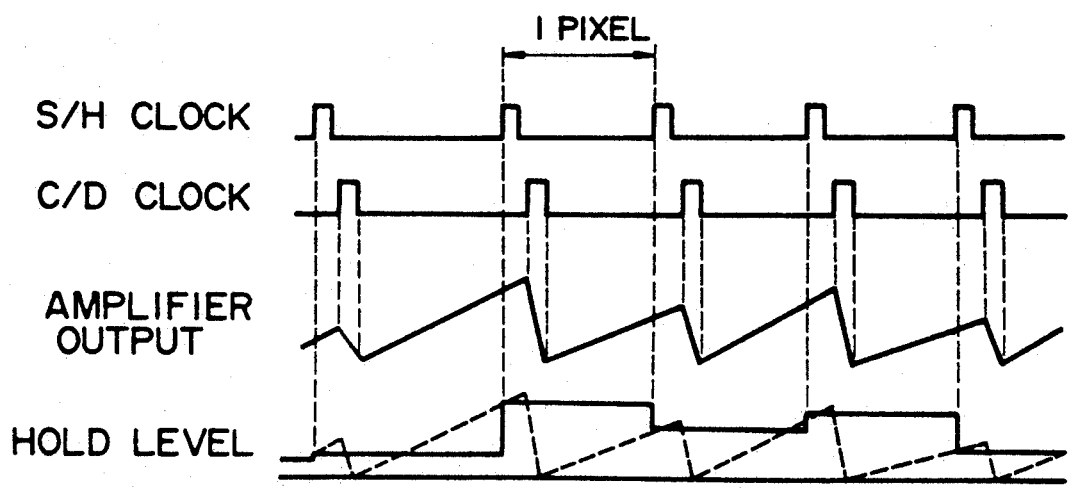
FIG. 9 is a time chart showing the timing of the reading operation of the amplifier.

The operation by the amplifier 25 containing the integral circuit as composed in the manner described hereinabove will be described with reference to the timing chart shown in FIG. 9. The output of the photomultiplier 24$f$ can be regarded nearly as a source of electric current because it has a very large output impedance. For the operational amplifier 25$a$, there may be employed a FET (field-effect transistor) of an input type having a high input impedance. Hence, when the switch 25$d$ is turned off, almost all the output current of the photomultiplier 24$f$ flows through the condenser 25$c$. This electric current makes the output voltage of the operational amplifier 25$a$ a ramp function type, as shown in FIG. 9. The integral operation proceeds for the period of time corresponding to one pixel and a sampling circuit located in the analog-digital converting circuit 26 performs sampling at the timing with a S/H clock and holds as it is, thereby allowing the analog-digital converting circuit 26 to make conversion into digital signals.

By activating a C/D clock serving as a C/D control signal to be added to the switch 25$d$ after holding, charges accumulated in the condenser 25$c$ are discharged. This operation is likewise repeated thereafter.

In the amplifying stages using the integral circuit, the charges from the photomultiplier 24$f$ can be integrated to a substantially complete extent, unlike a pseudointegral circuit composed of a resistance and a condenser alone. Hence, a high signal-to-noise ratio can be gained. Further, the integrating time can optionally be changed by changing the C/D clock of the C/D control signal to the switch 25$d$. Therefore, a degree of amplification for amplifying faint signals can readily be adjusted in a comprehensive way. In this example, the control can be performed in accordance with the area of the sample by making synchronization with the operation of the mirror driver 30 as shown in FIG. 4, thereby effectively taking advantage of the reading period of time. Further, the scanning time of the exciting light and the integrating time of the amplifier on the light-receiving side can be set with freedom in accordance with the intensity of the fluorescence from the sample, so that the apparatus can be composed in a very flexible manner.

As described hereinabove, the electric signals amplified by the amplifier (FIG. 2) are inputted into the analog-digital converting circuit 26 and converted into digital data. The detected signals of the fluorescence converted into the digital data are stored in the memory 28 and the data stored in the memory 28 are supplied to the data processor 8 through the interface circuit 29.

The overall control over a series of the signal processing is performed by the control circuit 27.

The following a description of the way of reading the electrophoresis pattern by using the electrophoresis pattern reading apparatus according to the embodiment of the present invention. In this case, the pattern obtained by developing the sample by electrophoresis is transcribed to a medium other than the gel.

It is to be noted that this procedure is applicable to the case in which it is difficult to label the sample with a fluorescent pigment. The order of the steps for reading is such that the sample labeled with no fluorescence is first separated by electrophoresis and a thin layer filter is then placed on the gel after the completion of the electrophoresis, followed by migrating the sample from the gel to the thin layer filter by taking advantage of the same principle as the electrophoresis. As the thin layer filter, there may be employed nitrocellulose, nylon or the like as a material surface-treated so as to readily adsorb the sample. Thereafter, a substance likely to adsorb the sample (hereinafter referred to as the "probe") is labeled with a fluorescent substance and adsorbed to the sample on the thin layer filter, followed by reading the electrophoresis pattern.

Figure 10:
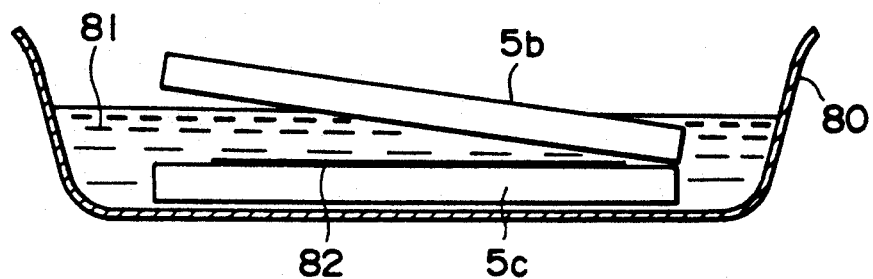
FIG. 10 is a diagram for describing the method for reading the sample transcribed to the thin layer filter.

FIG. 10 is a diagram for describing the process for reading the sample transcribed to the thin filter and labeled with the fluorescent probe.

The sample transcribed to the thin filter and labeled with the fluorescent probe can be read by directly installing the thin layer filter to the instrumentation unit 7. However, as the thin layer filter is white in itself, the light may be scattered to a strong extent so that the sensitivity to the fluorescence is lower, for example, by about one digit, than the case where the gel is employed. Hence, it may be hard to read the electrophoresis pattern if the sample would have a faint intensity of fluorescence.

Description is now turned to an example for processing the sample so as to suppress the intensity of the scattered light to a low level. As shown in FIG. 10, this process involves immersing the thin layer filter 82 in a buffer solution 81, the thin layer filter being treated by transcribing the electrophorezed sample to the thin layer film from the gel, adsorbing the probe labeled with the fluorescent substance to the electrophorezed sample. The thin layer filter 82 is interposed between the gel supporting members 5$b$ and 5$c$. In this case, attention should be paid so that as few bubbles as possible occur between the supporting members. The buffer solution 81 may be any one as long as it has an optical refractive index similar or identical to the gel supporting member or the thin layer filter and it does not cause any adverse influence upon the sample. The thin layer filter 82 is composed of a material having minute openings, however, the openings of the thin layer filter are covered with the buffer solution 81 so that the level of the light scattered can be reduced to a considerably small extent. The sample transcribed to the thin layer filter 82 and interposed by the gel supporting members 5$b$ and 5$c$ can be read by the instrumentation unit 7 in the same manner as the pattern of the sample obtained by electrophorezing the gel. Furthermore, the pattern can be read with a high S/N ratio by using the thin layer filter of non-fluorescence type.

Figure 11:
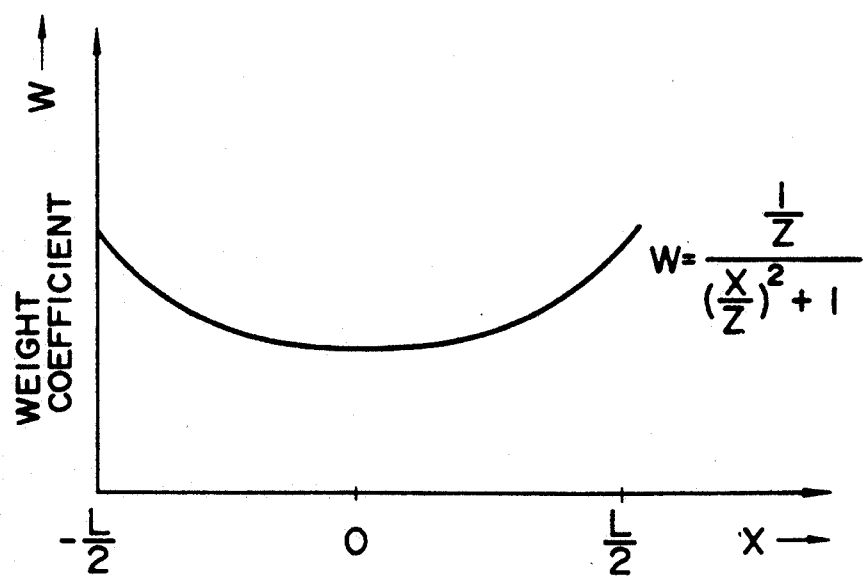
FIG. 11 is a diagram showing an example for performing the signal processing for the scanning correction by the optical scanning mechanism for scanning at equal angles with the mirror.
Figure 12:
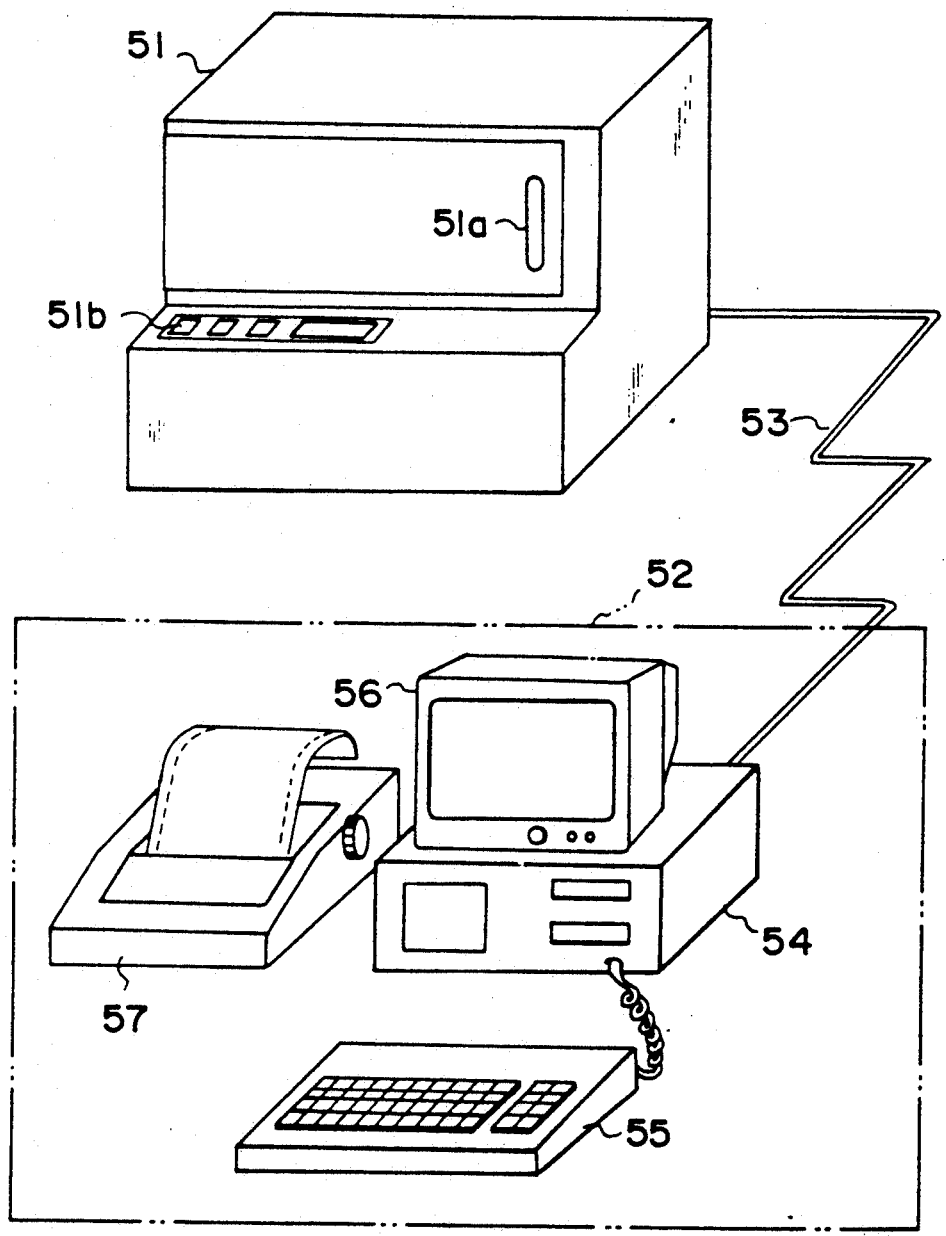
FIG. 12 is a perspective view showing the outlook of a conventional electrophoresis apparatus of a fluorescent type.
Figure 13:
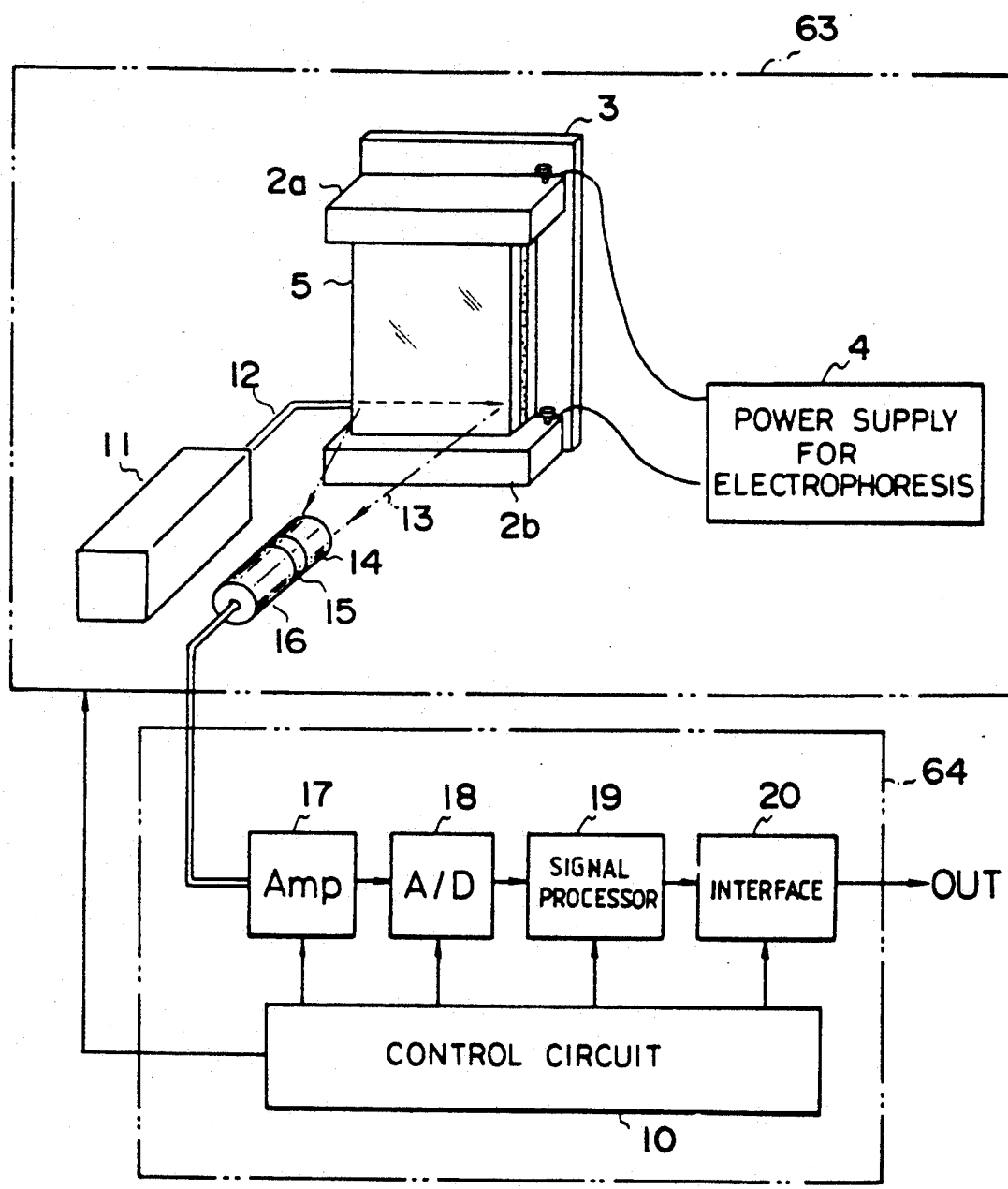
FIG. 13 is a block diagram showing the configuration of the inside of the electrophoresis and instrumentation units.

FIG. 11 is a diagram for describing an example for performing the signal processing by implementing scanning correction by the optical scanning mechanism for scanning at equal angles with the mirror. As shown in FIG. 4, when the vibrating mirror or a rotary polyhedral mirror is employed as the optical scanning mechanism, the angular velocity of rotating the mirror is not proportional to the velocity of scanning the surface of the electrophoresis unit so that the difference in sensitivity to the fluorescence occurs between the central portion and the side portions of the electrophoresis unit. Therefore, the mirror driver for the optical scanning mechanism of FIG. 4 is provided with a correction control circuit as shown in FIG. 6 so as to correct the velocity of the mirror driver for correcting the angular velocity of rotating the vibrating mirror. In place of this configuration, correction may be made in the stage of the data processing in which the electric signals of the fluorescence detected is data-processed by correcting characteristics of the fluorescence detecting sensitivity. In other words, in this case, the mirror is scanned at a constant speed (or at a constant angular velocity of rotation) and the intensity of the fluorescence read is corrected with a weight coefficient W in correspondence with the position W, in which the fluorescence has been detected, by taking advantage of the functional characteristic in which the intensity of the fluorescence read is a reverse function of the scanning velocity of the spot light, as shown in FIG. 11. Actually, it is preferred to correct the sensitivity, including other factors such as a variation in the power of laser and so on. In this example, the reading data is corrected while monitoring the power of the laser beams.

The present invention has been described with reference to specific embodiments, however, it should be understood that the present invention is construed as not restricted to those embodiments and as encompassing various modifications without departing from the spirit and scope of the invention.

As described hereinabove, the fluorescence pattern reading apparatus of fluorescence type according to the present invention enables the reading sensitivity to be set in a flexible manner in accordance with the size of the reading sample and the level of the strength of fluorescence by synchronizing the driving operation of the optical scanning mechanism for the exciting light when the exciting light is irradiated from the light source for reading the labels of the fluorescent pigment with the operation of the amplifier for performing the processing of the signals at the light-receiving unit. Further, the present invention enables the fluorescence pattern to be read with a high signal-to-noise ratio and allows a great improvement in a signal-to-noise ratio in the apparatus because it can reduce the level of the scattered light occurring from the thin layer filter when the sample is transcribed to the thin layer filter and the sample labeled with the fluorescence is read.

What is claimed is:

1. A fluorescence pattern reading apparatus for reading a fluorescence pattern by subjecting a sample, disposed between parallel transparent plates, to electrophoresis, developing the sample into an electrophoresis pattern, labeling the sample with a fluorescent substance and causing the fluorescence by exciting the fluorescent substance, comprising:

optical scanning means for irradiating the fluorescence pattern with an irradiation light for exciting the fluorescent substance of the fluorescence pattern in a direction substantially perpendicular to the major surfaces of the parallel transparent plates;

light receiving means, including a light-receiving surface, for receiving the fluorescence of the fluorescence pattern by separating the fluorescence from light scattered from a reading surface by means of a spatial relationship of a light-receiving path so set as to allow the light-receiving surface to exist in a direction different from a light axis of the irradiation light;

photoelectric converting means for outputting electric signals by photoelectrically converting optical signals received via the light-receiving means; and amplifier means for outputting electric signals of the fluorescence pattern in order by amplifying the electric signals from the photoelectric converting means by performing an integral operation in synchronization with the optical scanning of the irradiating light by the optical scanning means.

2. A fluorescence pattern reading apparatus as claimed in claim 1, wherein the amplifier means comprises an operational amplifier, a condenser and a switch for controlling the integral operation; and wherein the electric signals from the photoelectric converting means are subjected to integral amplification by the amplifier means by a portion corresponding to a reading pixel in order by controlling the synchronized integral operation of the amplifier means, thereby outputting the electric signals representing the fluorescence pattern.

3. A fluorescence pattern reading apparatus as claimed in claim 2, further comprising means for setting a range for reading the fluorescence pattern as an object for reading and a resolving capability for reading each pixel of the fluorescence pattern by controlling an integrating time and a holding period for holding a sample.

4. A fluorescence pattern reading apparatus as claimed in claim 1, wherein the optical scanning means comprises a vibrating mirror and a mirror driver for driving the vibrating mirror on the basis of a first control signal; and further comprising a control circuit for providing the first control signal to the mirror driver so as to allow a scanning velocity of a spot light of the irradiation light travelling on an irradiating surface which is exposed to the irradiation light to become substantially constant on the irradiating surface, said control circuit further providing a second control signal to the amplifier means so as to control the integral operation, said first and second control signals being provided so as to effect the synchronized optical scanning and integral operation.

5. A fluorescence pattern reading apparatus as claimed in claim 1, wherein:

the optical scanning means includes an optical scanning mechanism for providing a spot light of the irradiation light by scanning the irradiation light in a one-dimensional manner;

the optical scanning means further comprises a light-receiving unit for receiving light by condensing the fluorescence emitted from the fluorescent substance of the sample and correction processing means for correcting an intensity of the received fluorescence by means of changes in the spot light of the irradiation light; and wherein the fluorescence pattern reading apparatus further comprises:

means for amplifying and reading the electric signals representing the fluorescence received from the light-receiving unit after the intensity of the received fluorescence has been corrected by changes in the spot light of the irradiation light by the correction processing means; and means for controlling the optical scanning mechanism in synchronization with the integral operation.

6. A fluorescence pattern reading apparatus as claimed in claim 1, further comprising control means for controlling the synchronized integral operation and optical scanning.

* * * * *